United States Patent
Takahashi et al.

(10) Patent No.: US 11,320,399 B2
(45) Date of Patent: May 3, 2022

(54) GAS ANALYZER APPARATUS AND METHOD FOR CONTROLLING GAS ANALYZER APPARATUS

(71) Applicant: ATONARP INC., Tokyo (JP)

(72) Inventors: Naoki Takahashi, Tokyo (JP); Prakash Sreedhar Murthy, Tokyo (JP)

(73) Assignee: ATONARP INC., Tokyo (JP)

( * ) Notice: Subject to any disclaimer, the term of this patent is extended or adjusted under 35 U.S.C. 154(b) by 0 days.

(21) Appl. No.: 17/435,817

(22) PCT Filed: Mar. 24, 2020

(86) PCT No.: PCT/JP2020/012838
§ 371 (c)(1),
(2) Date: Sep. 2, 2021

(87) PCT Pub. No.: WO2020/196451
PCT Pub. Date: Oct. 1, 2020

(65) Prior Publication Data
US 2022/0042948 A1 Feb. 10, 2022

(30) Foreign Application Priority Data
Mar. 25, 2019 (JP) .............................. JP2019-057147

(51) Int. Cl.
*G01N 27/64* (2006.01)
*H01J 49/14* (2006.01)
*H01J 49/42* (2006.01)

(52) U.S. Cl.
CPC .............. *G01N 27/64* (2013.01); *H01J 49/14* (2013.01); *H01J 49/4215* (2013.01)

(58) Field of Classification Search
CPC ...... G01N 27/62; G01N 27/622; G01N 27/64; H01J 49/02; H01J 49/14; H01J 49/4215
See application file for complete search history.

(56) References Cited

U.S. PATENT DOCUMENTS 5,633,506 A 5/1997 Blake
7,894,037 B2 2/2011 Bleeker
(Continued)

FOREIGN PATENT DOCUMENTS

CN 1147690 A 4/1997
CN 103543614 A 1/2014
(Continued)

OTHER PUBLICATIONS

International Preliminary Report on Patentability (PCT/IPEA/409) issued in corresponding International Patent Application No. PCT/JJP2020/012838 dated Mar. 18, 2021. (3 pages).
(Continued)

*Primary Examiner* — David E Smith
(74) *Attorney, Agent, or Firm* — Buchanan Ingersoll & Rooney PC

(57) ABSTRACT

There is provided a gas analyzer apparatus that analyzes inflowing sample gas. The gas analyzer apparatus includes a filter unit that filters the sample gas, a detector unit that detects the result of filtering, a housing that houses these elements, and a control unit that controls the respective potentials of these elements. The control unit includes a cleaning control unit that sets the respective potentials of the filter unit, the detector unit, and the housing to cleaning potentials that draws in, as plasma for cleaning purposes, process plasma from a source that supplies the sample gas or plasma generated by a plasma generation unit.

13 Claims, 4 Drawing Sheets

(56) References Cited

U.S. PATENT DOCUMENTS

| | | | | |
|---|---|---|---|---|
| 2002/0139930 A1* | 10/2002 | Shiokawa | ............... | H01J 49/04 |
| | | | | 250/281 |
| 2005/0061444 A1 | 3/2005 | Noda | | |
| 2009/0014644 A1* | 1/2009 | Yang | ..................... | H01J 49/145 |
| | | | | 250/288 |
| 2016/0035550 A1* | 2/2016 | Perelman | ................ | H01J 49/00 |
| | | | | 250/282 |

FOREIGN PATENT DOCUMENTS

| | | | |
|---|---|---|---|
| CN | 106575598 A | 4/2017 | |
| JP | 2002298776 A | 10/2002 | |
| JP | 2010533933 A | 10/2010 | |
| JP | 2012003976 A | 1/2012 | |

OTHER PUBLICATIONS

International Search Report (PCT/ISA/210) with translation and Written Opinion (PCT/ISA/237) dated Jun. 2, 2020, by the Japanese Patent Office as the International Searching Authority for International Application No. PCT/JP2020/012838. (9 pages).

The First Office Action issued in corresponding Chinese Patent Application No. 202080024323.8, dated Feb. 11, 2022, with English Translation (23 pages).

* cited by examiner

GAS ANALYZER APPARATUS AND METHOD FOR CONTROLLING GAS ANALYZER APPARATUS

TECHNICAL FIELD

The present invention relates to a gas analyzer apparatus equipped with a cleaning function.

BACKGROUND ART

Japanese Laid-open Patent Publication No. 2012-3976 discloses a technology that provides a low-cost quadrupole mass spectrometer where a grid can be effectively degassed by impacting electrons without needing a separate power supply. An apparatus includes an ion source equipped with a filament and a grid, a quadrupole unit where four columnar electrodes are disposed at predetermined intervals in the circumferential direction, and an ion detector unit that collects predetermined ions that have passed through the quadrupole, and further includes: a power supply that passes a direct current through the filament; a power supply that applies a higher potential to the grid relative to the filament; a power supply that applies a predetermined potential to the filament to create a predetermined potential difference between the grid and the filament; a power supply that applies a voltage in which positive and negative DC voltages and an AC voltage have been superimposed to facing electrodes in the quadrupole unit; and a control unit. The apparatus is configured so that a voltage corresponding to the potential difference between the positive and negative voltages can be applied to the grid via the power supply provided for the quadrupole unit.

SUMMARY OF INVENTION

For applications such as monitoring of semiconductor manufacturing processes, there is demand for a highly durable sensor that can perform monitoring in various environments including a wide variety of gases.

One aspect of the present invention is a gas analyzer apparatus that analyzes inflowing sample gas. This apparatus includes: a filter unit that filters the sample gas; a detector unit that detects filtered results; a housing that houses the filter unit and the detector unit; and a control unit that controls respective potentials of the filter unit, the detector unit, and the housing. The control unit includes a cleaning control unit that sets the respective potentials of the filter unit, the detector unit, and the housing to cleaning potentials for drawing in, as plasma for cleaning purposes, one of process plasma of a source that supplies the sample gas and plasma generated by a plasma generation unit. The cleaning potentials may be ground potential and/or negative potentials. By setting, at regular or appropriate timing, the gas analyzer apparatus, including the housing, at the cleaning potentials, it is possible to draw in plasma and clean the inside of the gas analyzer apparatus with the drawn plasma.

The gas analyzer apparatus may include the plasma generation unit. The cleaning control unit may include a unit that sets the cleaning potentials at timing when the source that supplies the sample gas generates or provides the process plasma.

The gas analyzer apparatus may further include an ionization unit that ionizes the sample gas, and the filter unit may include a unit that filters the ionized sample gas. A typical example of a filter unit is a unit that performs filtering of ionized sample gas according to mass-to-charge ratio. The ionization unit may include a thermion supplying unit, and the cleaning control unit may include a unit that sets a potential of the ionization unit at one of the cleaning potentials to perform cleaning including the ionization unit.

Another aspect of the present invention is a method for controlling (control method of) a gas analyzer apparatus that analyzes an inflowing sample gas. The gas analyzer apparatus includes a filter unit that filters the sample gas, a detector unit that detects filtered results, a housing that houses the filter unit and the detector unit, and a control unit that controls respective potentials of the filter unit, the detector unit, and the housing. The control method includes setting cleaning potentials, by the control unit, as the respective potentials of the filter unit, the detector unit, and the housing for drawing in, as plasma for cleaning purposes, one of process plasma of a source that supplies the sample gas and plasma generated by a plasma generation unit. The cleaning potentials may be selected from among ground potential and negative potentials.

The gas analyzer apparatus may include the plasma generation unit, and the method may further include generating the cleaning plasma, by the plasma generation unit, in parallel with the setting cleaning potentials. The setting cleaning potentials may include setting the cleaning potentials at timing when the source that supplies the sample gas provides the process plasma. When the gas analyzer apparatus includes an ionization unit that ionizes the sample gas, the setting cleaning potentials may include setting a potential of the ionization unit at one of the cleaning potentials.

Another aspect of the present invention is a program that controls a gas analyzer apparatus which analyzes an inflowing sample gas. The program (or program product) includes instructions that have the control unit set the respective potentials of a filter unit, a detector unit, and a housing to cleaning potentials for drawing in, as plasma for cleaning purposes, process plasma of a source that supplies the sample gas or plasma generated by a plasma generation unit. The program or program product may be provided having been recorded on a suitable recording medium.

DETAIL DESCRIPTION OF THE INVENTION

One embodiment of the present invention is a gas analyzer apparatus, and one example of this is a mass spectrometry apparatus. In applications such as monitoring of semiconductor manufacturing processes, it is necessary to monitor gases that include a wide variety of components, and there is demand for sensors that can measure these gases stably and with high accuracy.

Figure 1:
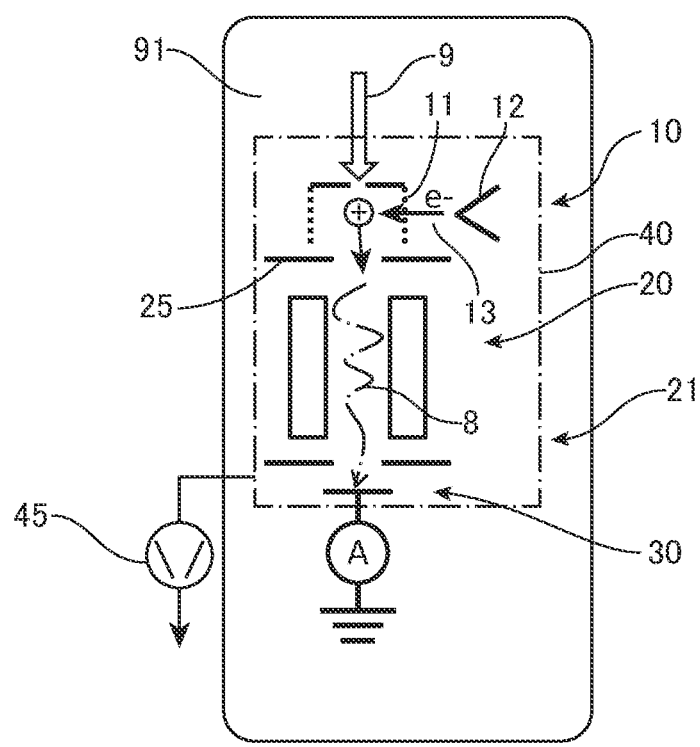
FIG. 1 is a block diagram depicting one example of a conventional mass spectrometry apparatus.

As one example of a gas analyzer apparatus, an overview of a quadrupole mass spectrometer will now be described with reference to FIG. 1. A quadrupole mass spectrometer (mass spectrometry apparatus, mass spectrometer) 91 includes an ionization apparatus (ionization unit, ionizer or ion source) 10 that ionizes gas (gas samples or sample gases) 9 to be analyzed and a gas analyzer unit (gas analyzer section, gas analyzer) 21 that analyzes ionized gas 8. The gas analyzer unit 21 includes a quadrupole unit 20, which is a filter unit, and a detector unit (detector, detection unit, as one example, a Faraday cup) 30 that collects gas ions 8 that have arrived after passing between the electrodes of the quadrupole. The filter unit (filter) 20 includes a plurality of, typically four, columnar electrodes that extend vertically and are disposed at predetermined intervals in the circumferential direction. The mass spectrometry apparatus 91 includes a vacuum vessel (housing) 40, which houses or receives the ionization apparatus 10, the filter unit 20, and the detector unit 30, and a vacuum pump 45 that keeps the inside of the housing 40 at negative pressure. Gas 9 that has flowed into the housing 40 is ionized by the ionization apparatus 10.

The ionization apparatus 10 includes a grid 11 and a filament 12 that functions as a cathode for supplying an electron flow. One example of the grid 11 is constructed by arranging thin metal wires into a grid that is cylindrically shaped. The filament 12 is connected to metal support pins installed at predetermined intervals in the circumferential direction on a support frame, and is disposed around the outside of the grid 11. As one example, the filament 12 is produced by coating the surface of a base material made of iridium with yttrium oxide by performing an electrodeposition treatment. A focusing electrode 25 is interposed between the filter unit 20 and the ionization unit 10 so that ions that are headed toward the filter unit 20 efficiently converge. As one example, the focusing electrode 25 is electrically connected to the support pins of the filament 12 so that the potential of the filament 12 and the potential of the focusing electrode 25 become equal.

A conventional mass spectrometry apparatus 91 is designed so as to operate in an environment of pure gas as a condition, that is, an environment that does not include corrosive gas. One example of a cathode material (filament material) suited to this condition is a $Y_2O_3$/Ir filament, where the core material is made of iridium (Ir) and the electron emitting layer is made of yttrium oxide (yttria, $Y_2O_3$). Tungsten (W) materials are believed to be effective as the filament material (cathode material) for gases that contain fluorocarbons CFx as components.

In environments where the gas from the process includes silicon oil, the filament 12 will become coated with silicon (Si), silicon oxide ($SiO_2$), silicon nitride (SiN), or the like, especially when the mass spectrometer 91 starts or stops, which may impair functioning.

At present, inconel 600 is often used as the grid 11. Part of the gas may become deposited on the grid 11 to form an insulating film, and due to this the correct potential distribution may not be created in the ionizer/ion optical region. One of examples of processes to be monitored by the gas analyzer apparatus 91 is a system that performs CVD or PVD during a semiconductor manufacturing process. The processes performed by such systems may include processes of depositing oxide or an insulator, such as silicon dioxide ($SiO_2$), silicon nitride ($SiN_3$), titanium nitride (TiN), or tantalum nitride (TaN), and in the gas analyzer apparatus 91 that monitors these systems, these oxides or insulators can become deposited on the ionization unit 10, the filter unit 20, the detector unit 30, and/or the housing 40.

Figure 2:
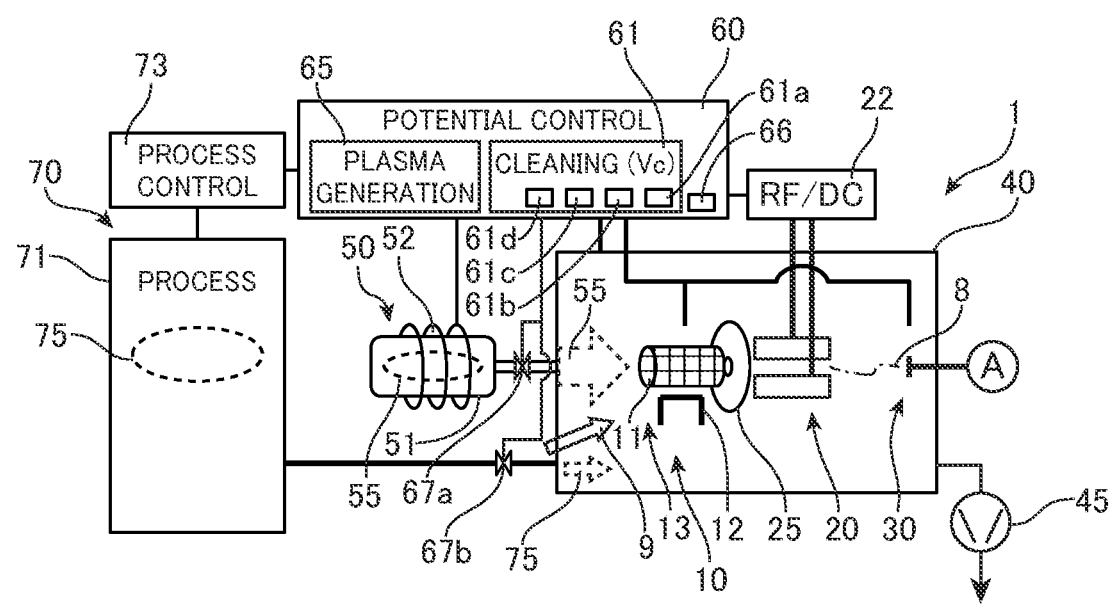
FIG. 2 is a diagram depicting an example of a gas analyzer apparatus that performs plasma cleaning.

FIG. 2 depicts one embodiment of the present invention. This gas analyzer apparatus (gas analyzing apparatus, gas analyzer) 1 is a mass spectrometry apparatus (mass spectrometer) like the gas analyzer apparatus depicted in FIG. 1, and is an apparatus that analyzes a sample gas 9 that flows into the housing 40 from a process 70. The gas analyzer apparatus 1 includes an ionization unit 10 that ionizes the sample gas 9, a filter unit (in this example, a quadrupole unit, a quadrupole filter) 20 that filters the ionized sample gas (ionized gases, gas ions) 8 according to mass-to-charge ratio, a focusing electrode 25, a detector unit (detector) 30 that detects ions (gas components) that have passed through the filter unit 20 as a result or results of the filtering, and the housing (chamber) 40 that houses or receives the ionization unit 10, the filter unit 20, and the detector unit 30 and performs control so that the inside is kept at negative pressure by a vacuum pump or pumps 45. The gas analyzer apparatus 1 further includes a control unit (controller) 60 that controls the potentials (electric or electrical potentials) of the ionization unit 10, the focusing electrode 25, the filter unit 20, the detector unit 30, and the housing 40 respectively. The potential of the filter unit 20 is controlled via a driving unit (RF/DC unit) 22 that applies a high frequency and direct current to the quadrupole. The ionization unit 10 includes a filament (cathode) 12 and the grid 11 as a thermion (thermal electrons) supplying unit 13.

The gas analyzer apparatus 1 includes a plasma generation unit (plasma generator) 50 that generates plasma 55 for cleaning purposes. One example of the plasma generation unit 50 is a unit capable of generating plasma at a low pressure of around 0.01 to 1 kPa using a generation method that does not use electrodes. The plasma generation unit 50 includes a vessel 51 formed of a dielectric material with high durability against plasma, such as quartz, aluminum oxide ($Al_2O_3$), or silicon nitride ($SiN_3$), and a mechanism 52 for generating plasma in the vessel using an electric field and/or a magnetic field. The plasma generation unit 50 can draw in gas or gases from the processes or gases with components suited for cleaning and generate plasma under a pressure of 0.01 to 1 kPa using a method such as inductively coupled plasma (ICP), dielectric barrier discharge (DBD), or electron cyclotron resonance (ECR) and others. As one example, when this plasma generation also serves for measurement purposes, the plasma may be generated under a reduced pressure of around 1 to 10 mTorr. When the plasma is generated exclusively for cleaning, the plasma may be generated under a pressure of around ten to several hundred Pa. A magnetic field and an electric field may be used together to confine the plasma inside the vessel.

The control unit 60 controls the potentials of each part of the gas analyzer apparatus 1. When analyzing the sample gas 9, the potential of the grid 11 in the ionization unit 10 is set so that an electron flow (thermion flow) of a predetermined energy (eV) with respect to the potential of the filament (cathode) 12 is obtained. As one example, the potential of the grid 11 is set at 5 to 15V and the potential of the filament 12 is set at 20 to 100V with respect to the potential of the grid 11 to produce a negative voltage. Note that these potentials are examples, and the present invention is not limited to these values. The same applies to the following description. The sample gas or gases 9 collides with the thermion flow (thermal electron flow) supplied from the filament 12 in the ionization unit 10 to become gas ions (cations) 8, and part of the sample gas 9 is drawn by the extraction electrode (focusing electrode) 25 and supplied to the filter unit 20.

As the potential of the filter unit 20, a voltage with opposite polarity produced by superimposing a DC component and a high frequency component is applied via the driving unit 22. The potential of the ion detector unit 30 that uses a Faraday cup or the like is set at a potential that is lower than the potential of the grid 11, as examples, ground potential or a slightly negative potential, to detect the gas ions 8 that have passed or been led through the filter unit 20. The potential of the housing 40 that houses these elements is set at ground potential or a positive potential to suppress the influence of the housing 40 on the ion flow 8.

The control unit 60 includes a cleaning control unit (cleaning controller) 61 that draws plasma into the entire gas analyzer apparatus 1 and specifically the housing 40 to clean not only the parts housed inside the housing 40 but also the housing 40 itself. The cleaning control unit 61 sets the potential of the thermion supplying unit 13 including the grid 11 and the filament 12 of the ionization unit 10, the potential of the filter unit 20, the potential of the detector unit 30, and the potential of the housing 40 at cleaning potentials Vc and maintains the respective cleaning potentials Vc during cleaning. That is, the cleaning control unit 61 includes a unit 61a that sets the potential of the filter unit 20, the detector unit 30, and the housing 40 to the cleaning potentials Vc respectively, and a unit 61b that sets the potential of the ionization unit 10 at one of the cleaning potentials Vc.

The cleaning potentials Vc may be set from among ground potential or negative potentials so as to effectively draw in the plasma, which is positively charged, and thereby raise the efficiency of the plasma cleaning. Plasma is often positively charged to several volts or so, and it is therefore desirable for the cleaning potentials Vc to be negative potentials so as to efficiently draw the plasma into the housing 40 and perform cleaning.

Further, the cleaning control unit 61 may set the cleaning potentials Vc having the same potential for the ionization unit 10, the filter unit 20, the detector unit 30, and the housing 40, or may set the respective potentials as cleaning potentials Vc to form a suitable voltage gradient in order to draw in plasma more effectively. As one example, the cleaning potentials Vc may be set to form a voltage gradient that aims toward the housing 40. For purposes such as achieving concentrated cleaning effects during cleaning or controlling the intensities of the cleanings, for each section out of the ionization unit 10, the filter unit 20, the detector unit 30, and the housing 40, or for the component parts that construct respective sections, the respective cleaning potentials Vc may be controlled sequentially or randomly over time to control the one or more potentials and/or one or more potential differences at each section and/or component. The respective cleaning potentials Vc may also be changed or varied during cleaning for the system as a whole or in units of the respective sections or respective components.

The control unit 60 includes a plasma generation control unit (plasma generation controller) 65 that generates plasma in the plasma generation unit 50 at the timing where the cleaning plasma 55 is required. The cleaning control unit 61 includes a unit 61c that periodically determines the need for plasma cleaning, for example in keeping with monitoring results for the performance of the gas analyzer apparatus 1, such as changes in the emission current from the filament 12 of the ionization unit 10, in response to an order from an application on a higher-level than the gas analyzer apparatus 1 and in other reasons.

When the cleaning control unit 61 determines that plasma cleaning is necessary, the plasma generation unit 50 generates plasma 55 for cleaning purposes via the plasma generation control unit 65. When the cleaning potentials Vc are set, the generated plasma 55 is drawn through the ionization unit 10 until the plasma 55 comes into contact with the filter unit 20, the detector unit 30 and the housing 40, to remove substances adhering to the surfaces of these elements, for example, insulating substances such as oxides.

The plasma 55 generated in the plasma generation unit 50 is charged a certain amount, around several Volts or so and as one example, a positive potential of about 5 V. This means that by keeping the gas analyzer apparatus 1 at the cleaning potentials Vc which are the ground potential and/or negative potentials, the plasma 55 can be drawn inside the gas analyzer apparatus (mass spectrometry apparatus) 1 and perform plasma cleaning. The potentials of the gas analyzer apparatus 1 during cleaning may be lower than the potential of the plasma 55 and may be a positive potential, but since it is preferable to maintain a certain potential difference with respect to the potential of the plasma 55, the cleaning potentials Vc may be selected from among the ground potential and negative potentials below the ground potential. The potential of the plasma 55 for cleaning purposes generated in the plasma generation unit 50 may be further raised and set at a positive potential that is high with respect to that of the ionization unit 10, the filter unit 20, the detector unit 30, and the housing 40. In this case, even if the cleaning potentials Vc may be set at positive potentials during cleaning, it will still be possible to draw the plasma 55 for cleaning into the gas analyzer apparatus 1, and more specifically, into the housing 40, and perform cleaning.

The cleaning control unit 61 includes a unit (process plasma cleaning unit, process plasma cleaner) 61d that sets the cleaning potentials Vc at the timing when the process 70, which is the source of the sample gas 9, generates or provides the process plasma 75. The process 70 to be monitored by the gas analyzer apparatus (mass spectrometry apparatus) 1 may include a system 71 that performs CVD (Chemical Vapor Deposition) and/or PVD (Physical Vapor Deposition). The system 71 may include processes of depositing an oxide or an insulator, such as silicon oxide ($SiO_2$), silicon nitride ($SiN_3$), titanium nitride (TiN), and tantalum nitride (TaN). In such processes, TEOS (tetraethyl orthosilicate) plasma is used for $SiO_2$ process, and plasma containing silane ($SiH_4$) and ammonia ($NH_3$) is used for SiN process. Accordingly, it is possible to clean the inside of the gas analyzer apparatus 1 by drawing these process cleaning plasmas into the gas analyzer apparatus 1, when used or provided, as the cleaning plasma 75.

When the process that is the source of the sample gas 9 for monitoring is a semiconductor manufacturing process 70, etching plasma will be generated or provided for purposes such as cleaning the inside of the system 71 or dry etching the workpieces of the process 70. As one example, cleaning plasma 75 including fluorocarbon (CFx), sulfur hexafluoride ($SF_6$), nitrogen trifluoride ($NF_3$), silicon tetrafluoride ($SiF_4$), or the like that generate fluorine-based radicals is generated. The process plasma cleaning unit 61d of the cleaning control unit 60 communicates with a process control unit (process controller) 73 that controls the system 71 of the process 70, and acquires the timing at which the system 71 generates the plasma 75 for process cleaning or plasma for dry etching. The cleaning control unit 61 sets the cleaning potentials Vc at this timing.

Accordingly, it allows the gas analyzer apparatus 1 to clean itself inside by changing from the potentials set for monitoring purposes to the cleaning potentials Vc in accordance with the timing at which the cleaning plasma 75 is provided or generated by the process 70 being monitored by the gas analyzer apparatus 1. This means that when the process 70 restarts, the gas analyzer apparatus 1 is able to start monitoring the process 70 with the gas analyzer apparatus 1 in a refreshed state. When a plurality of gas analyzer apparatuses 1 are disposed for monitoring the process 70, it is also possible to switch between the plurality of gas analyzers 1 according to time division and draw plasma 75 from the process 70 to clean the insides of the respective gas analyzer apparatuses 1.

If the time (i.e., amount of time) and/or timing required to clean the system 71 does not match the time (i.e., amount of time) and/or timing required to clean the insides of the individual gas analyzer apparatuses 1, it is possible to provide a control valve (shutoff valve) 67b on the line (pipe) into which the sampling gas 9 and the cleaning plasma 75 flow and have the cleaning control unit 61 control the introduction of the cleaning plasma 75. A control valve (shutoff valve) 67a may be provided on the line (pipe) that introduces the cleaning plasma 55 from the plasma generation unit 50 and the cleaning control unit 61 may control the introduction of the cleaning plasma 55.

Many parts of the gas analyzer apparatus 1 are made of metal, and oxides and various other substances with insulating properties may be deposited by the gas 9 being measured. As examples, when monitoring CFx (of a low concentration), Fluorine may become separated as a gas and the carbon (C) may be deposited, while when monitoring TEOS, $SiO_2$ may be deposited. On the other hand, if cleaning plasma 55 or 75 such as CFx is introduced to clean the metal surfaces, the metal may corrode, which would shorten the life of the gas analyzer apparatus 1. For this reason, it is effective to use pyrolytic carbon (pyrolytic graphite (PG)) instead of metal or to attach or coat PG onto metal surfaces, including the inner surfaces of the housing 40, that construct the gas analyzer apparatus 1.

Figure 3:
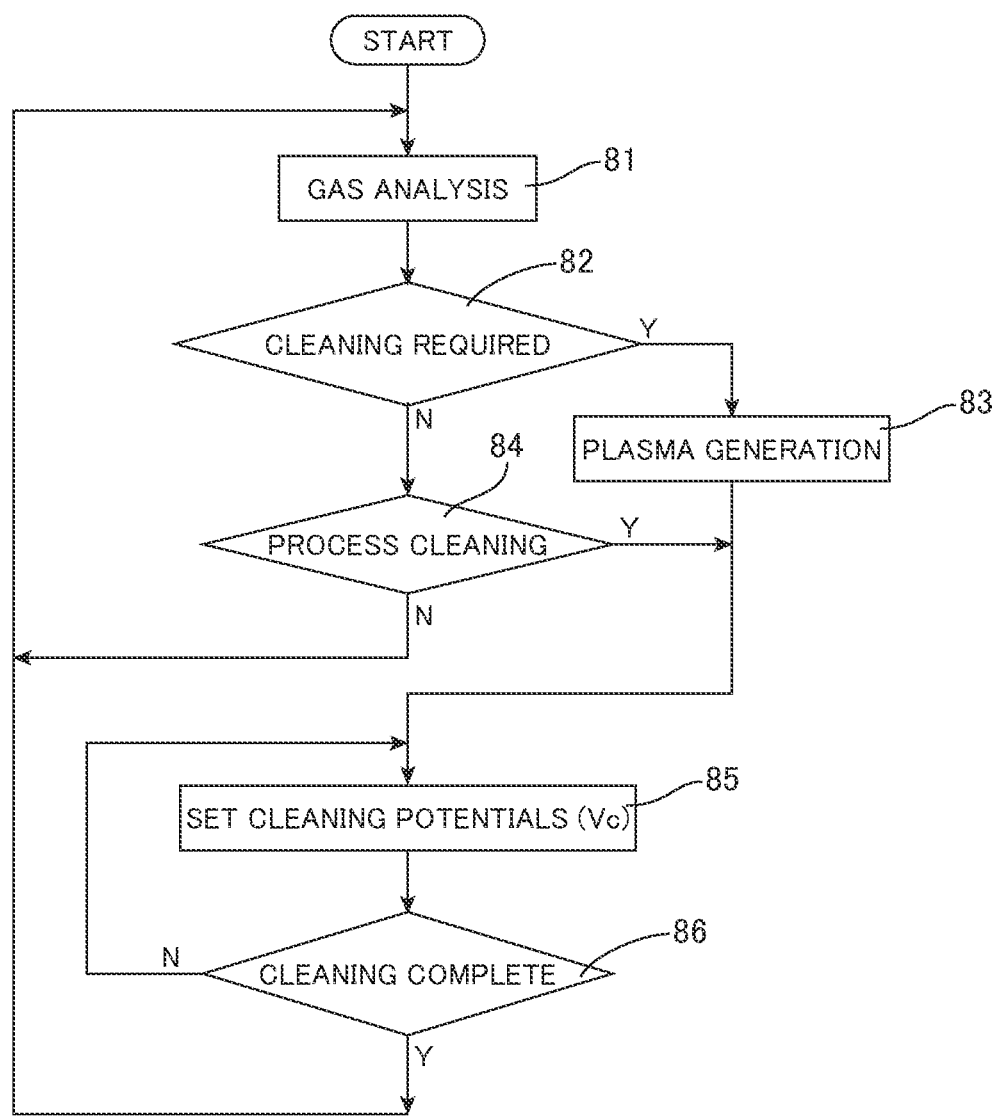
FIG. 3 is a flowchart depicting an overview of control of the gas analyzer apparatus.

FIG. 3 depicts one of examples of the control method for the gas analyzer apparatus 1. In step 81, the control unit 60 sets the respective potentials of each section and each element of the gas analyzer apparatus 1, including the ionization unit 10, the filter unit 20, the detector unit 30, and the housing 40 in a measurement state, and performs analysis of the sample gas 9 that flows in from the process 70. When the cleaning control unit 61 has determined, in step 82, that cleaning is required or necessary based on information such as the running time of the gas analyzer apparatus 1 or the monitoring results of the respective internal sections, in step 83, the plasma generation unit 50 generates the cleaning plasma 55. In step 85, the cleaning control unit 61 sets the cleaning potentials Vc. In parallel with this, in step 85, the plasma generation unit 50 generates the cleaning plasma 55 and the gas analyzer apparatus 1 draws in the cleaning plasma 55 to perform cleaning, including the housing 40.

On the other hand, in step 84, when the cleaning control unit 61 has communicated with the process control unit 73 and determined that it is time for the process 70 to commence cleaning and generate or provide the cleaning plasma 75, in step 85, the cleaning potentials Vc are set and the cleaning plasma 75 is drawn in from the process 70 to clean the gas analyzer apparatus 1. The cleaning control unit 61 maintains the cleaning potentials Vc until the cleaning is completed in step 86. When the cleaning has been completed, the processing returns to step 81 to commence gas analysis.

The functions of the control unit 60 including the cleaning control unit 61 may be provided by a program (program product) 66 that includes instructions for executing the above setting processes of the cleaning potentials Vc. The control unit 60 may include computer resources, such as a processor, a memory and others, and the program 66 may be recorded and provided on a recording medium, such as a memory.

Figure 4:
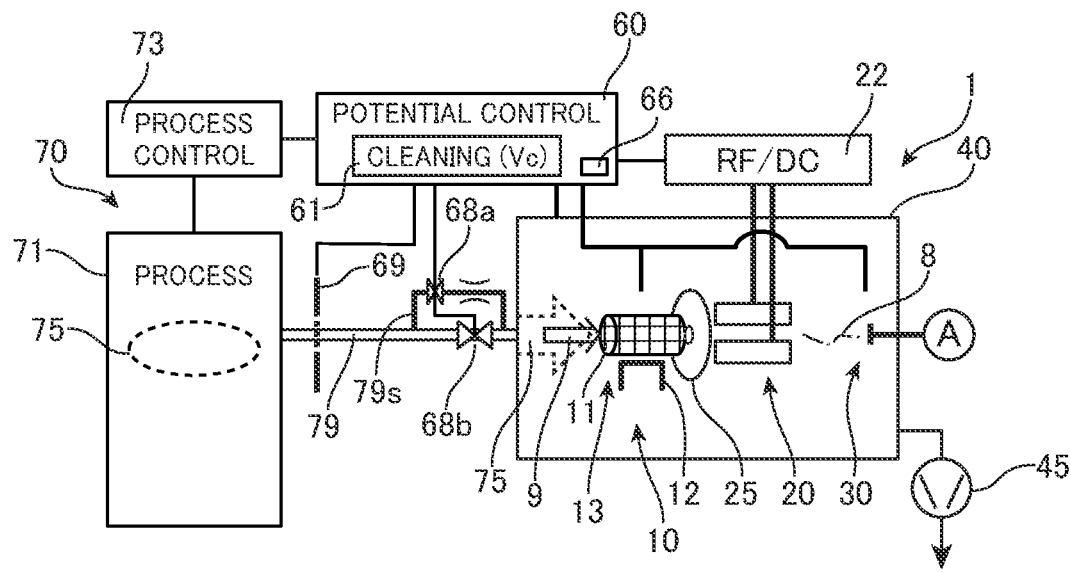
FIG. 4 is a diagram depicting another example of a gas analyzer apparatus that performs plasma cleaning.

FIG. 4 depicts another embodiment of the present invention. The basic configuration of this gas analyzer apparatus (mass spectrometry apparatus, mass spectrometer) 1 is the same as that of the gas analyzer apparatus shown in FIG. 2. The ionization unit 10 includes a filament 12 and a grid 11 as a thermion supplying unit 13. The gas analyzer apparatus 1 of this embodiment does not include the plasma generation unit 50, but includes a cleaning control unit 61 that performs cleaning by drawing in cleaning plasma 75 generated by the process 70 being monitored. Accordingly, the cleaning control unit 61 communicates with the process control unit 73, and when the timing where the process 70 generates or provides the cleaning plasma 75 is reached, sets the respective cleaning potentials Vc for each section and each part, including the housing 40, of the gas analyzer apparatus 1 and draws the cleaning plasma 75 via the sampling line 79 into the gas analyzer apparatus 1.

The gas analyzer apparatus 1 may be equipped with an extraction electrode 69 whose potential is set so as to extract the cleaning plasma 75 from the process 70. A line (pipe) 79 with a large diameter compared to the line (pipe) 79s for supplying the sampling gas 9 may be provided for supplying the cleaning plasma 75. When the cleaning plasma 75 is drawn in, the cleaning control unit 61 may automatically perform an operation that closes a valve 68a on the sampling line 79s and opens a valve 68b on the plasma supplying line 79.

Figure 5:
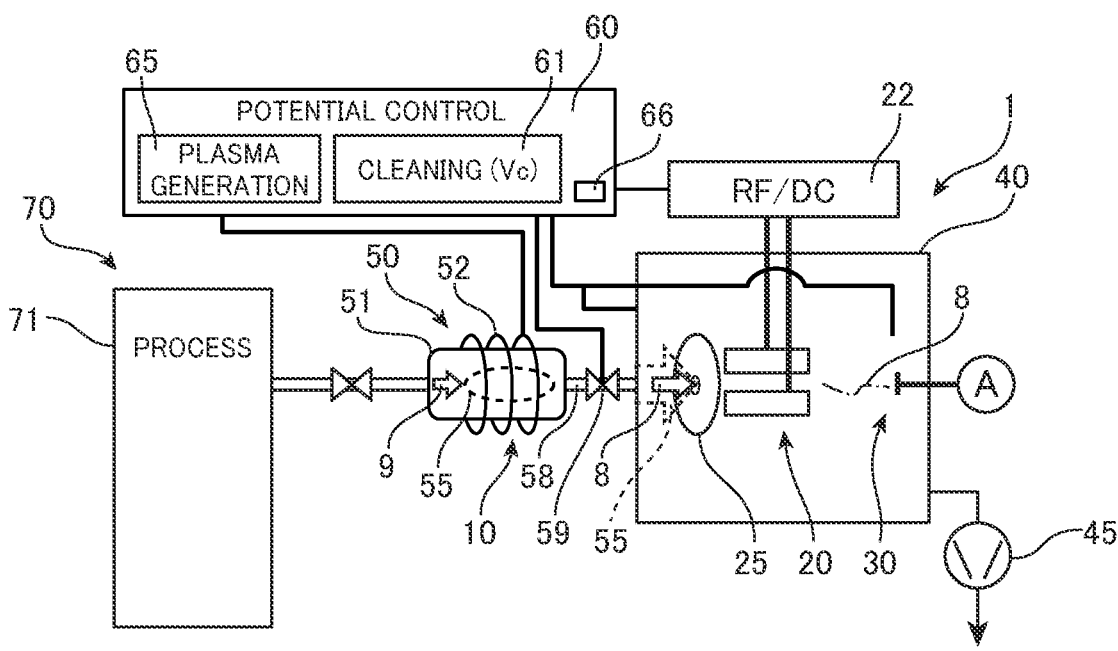
FIG. 5 is a diagram depicting yet another example of a gas analyzer apparatus that performs plasma cleaning.

FIG. 5 depicts yet another embodiment of the present invention. The basic configuration of this gas analyzer apparatus 1 (mass spectrometry apparatus, mass spectrometer) 1 is the same as that of the gas analyzer apparatus depicted in FIG. 2. As the ionization unit 10, in place of the thermion supplying unit 13, the plasma generator 50 converts the sample gas 9 from the process 70 into the plasma 55 and supplies the plasma 55 to the filter unit 20 as an ion flow 8 for gas analysis purposes. When the cleaning control unit 61 has determined that cleaning is required, the cleaning control unit 61 sets the filter unit 20, the detector unit 30, and the housing 40 at the cleaning potentials Vc respectively so that a large amount of plasma 55 generated by the plasma generation unit 50 is drawn into the housing 40 as the cleaning plasma 55.

It is also possible to provide a control valve 59 on the plasma supply line 58 that connects the plasma generation unit 50 and the housing 40 and to control the degree of opening of the valve 59 via the cleaning control unit 61 to control the amount of plasma supplied to the housing 40. In the same way as the gas analyzer apparatus depicted in FIG. 4, it is possible to switch between two lines with different diameters to control the amount of plasma supplied to the housing 40.

Note that although a quadrupole-type mass spectrometer has been described above as an example, the filter unit 20 may be an ion trap or another type of filter, such as a Wien filter. The filter unit 20 is not limited to a mass spectrometry-type, and may be a filter that filters molecules or atoms of a gas or gases using other physical quantities, such as ion mobility.

Although specific embodiments of the present invention have been described above, various other embodiments and modifications will be conceivable to those of skill in the art without departing from the scope and spirit of the invention. Such other embodiments and modifications are addressed by the scope of the patent claims given below, and the present invention is defined by the scope of these patent claims.

The invention claimed is:

1. A gas analyzer apparatus that analyzes inflowing sample gas and comprises:
   a filter unit that filters the sample gas;
   a detector unit that detects filtered results;
   a housing that houses the filter unit and the detector unit; and
   a control unit that controls respective potentials of the filter unit, the detector unit, and the housing,
   wherein the control unit includes a cleaning control unit that sets the respective potentials of the filter unit, the detector unit, and the housing to cleaning potentials for drawing in, instead of potentials for analyzing that lead ions to the detector unit, as plasma for cleaning purposes, one of process plasma of a source that supplies the sample gas and plasma generated by a plasma generation unit, and
   the cleaning potentials include potentials for forming a voltage gradient that aims toward the housing for drawing in the plasma by setting the respective potentials of the filter unit, the detector unit and the housing.

2. The gas analyzer apparatus according to claim 1, wherein the cleaning control unit sets a cleaning potential of the housing to a negative potentials.

3. The gas analyzer apparatus according to claim 1, further comprising the plasma generation unit.

4. The gas analyzer apparatus according to claim 1, wherein the cleaning control unit includes a unit that sets the cleaning potentials at a timing when the source that supplies the sample gas provides the process plasma.

5. The gas analyzer apparatus according to claim 1, further comprising an ionization unit that ionizes the sample gas,
   wherein the filter unit includes a unit that filters the ionized sample gas.

6. The gas analyzer apparatus according to claim 5, wherein the ionization unit includes a thermion supplying unit, and
   the cleaning control unit includes a unit that sets a potential of the ionization unit at one of the cleaning potentials.

7. The gas analyzer apparatus according to claim 5, wherein the ionization unit includes the plasma generation unit.

8. A method for controlling a gas analyzer apparatus that analyzes an inflowing sample gas,
   the gas analyzer apparatus including a filter unit that filters the sample gas, a detector unit that detects filtered results, a housing that houses the filter unit and the detector unit, and a control unit that controls respective potentials of the filter unit, the detector unit, and the housing, and
   the method comprising setting cleaning potentials, by the control unit, as the respective potentials of the filter unit, the detector unit, and the housing, instead of potentials for analyzing that lead ions to the detector unit, the cleaning potentials being for drawing in, as plasma for cleaning purposes, one of process plasma of a source that supplies the sample gas and plasma generated by a plasma generation unit,
   wherein the cleaning potentials include potentials for forming a voltage gradient that aims toward the housing for drawing in the plasma by setting the respective potentials of the filter unit the detector unit and the housing.

9. The method according to claim 8, where the setting cleaning potentials includes setting a cleaning potential of the housing to a negative potentials.

10. The method according to claim 8, wherein the gas analyzer apparatus includes the plasma generation unit, and
    the method further comprises generating the cleaning plasma, by the plasma generation unit, in parallel with the setting the cleaning potential.

11. The method according to claim 8, wherein the setting cleaning potentials includes setting the cleaning potentials at timing when the source that supplies the sample gas provides the process plasma.

12. The method according to claim 8, wherein the gas analyzer apparatus includes an ionization unit that ionizes the sample gas, and the filter unit includes a unit that filters the ionized sample gas, and
    the setting cleaning potentials includes setting a potential of the ionization unit at one of the cleaning potentials.

13. A program that controls a gas analyzer apparatus that analyzes an inflowing sample gas,
    the gas analyzer apparatus including a filter unit that filters the sample gas, a detector unit that detects filtered results, a housing that houses the filter unit and the detector unit, and a control unit that controls respective potentials of the filter unit, the detector unit, and the housing, and
    the program comprising instructions for having the control unit set the respective potentials of the filter unit, the detector unit, and the housing to cleaning potentials for drawing in, instead of potentials for analyzing that lead ions to the detector unit, as plasma for cleaning purposes, one of process plasma of a source that supplies the sample gas and plasma generated by a plasma generation unit,
    wherein the cleaning potentials include potentials for forming a voltage gradient that aims toward the housing for drawing in the plasma by setting the respective potentials of the filter unit, the detector unit and the housing.

* * * * *